United States Patent [19]

Peradze et al.

[11] 4,071,619
[45] Jan. 31, 1978

[54] METHOD OF PRODUCING VACCINES

[76] Inventors: Tamaz Vladimirovich Peradze, ulitsa Basseinaya, 53, kv. 353; Eidlya Abramovna Fridman, ulitsa Rudischeva, 19, kv. 2; Nina Vsevolodovna Zheleznova, ulitsa Khalturina, 13, kv.; Vsevolod Mikhailovich Kolikov, prospekt Engelsa, 100, kv. 59; Semen Khaimovich-Efimovich Bresler, Lesnoi prospekt, 61, kv. 244; Boris Viktorovich Mchedlishvili, Novoizmailousky prospekt, 3, kv. 211; Viktor Mikhailovich Molodkin; Ljudmila Mikhailovna Molodkina, both of prospekt Shaumiana, 2, kv. 11; Nina Vasilievna Katushkina, Novoizmailovsky prospekt, 4, kv. 245, all of Leningrad, U.S.S.R.

[21] Appl. No.: 719,692

[22] Filed: Sept. 2, 1976

Related U.S. Application Data

[63] Continuation of Ser. No. 523,363, Nov. 13, 1974, abandoned.

[30] Foreign Application Priority Data

Nov. 16, 1973 U.S.S.R. .............................. 1967101

[51] Int. Cl.$^2$ .................... A61K 41/00; A61K 39/12; C12K 7/00
[52] U.S. Cl. ...................................... 424/90; 195/1.5; 424/89
[58] Field of Search ...................... 195/1.5; 424/89, 90

[56] References Cited

PUBLICATIONS

Haller – Nature – vol. 204 (May 15,1965) pp. 693-696.

*Primary Examiner*—Sam Rosen
*Attorney, Agent, or Firm*—Haseltine, Lake & Waters

[57] ABSTRACT

A method for producing vaccines wherein a suspension of the viral culture is purified by gel chromatography in a column packed with a porous virion non-sorbing silicate material having pore diameter of 50 to 10000 A, followed by adsorption-elution concentration and completion of the vaccine, or the starting suspension of the viral culture is concentrated by adsorption-elution and then purified by gel chromatography in a column packed with porous silicate material having pore diameter of 50 to 10000 A, or the starting suspension of the viral culture is subjected to gel chromatography in a column filled with a porous silicate material having pore diameter of 50 to 10000 A and the final vaccine is produced.

8 Claims, No Drawings

METHOD OF PRODUCING VACCINES

This is a continuation of U.S. patent application Ser. No. 523,363, filed Nov. 13, 1974, now abandoned.

The present invention relates to a method for producing vaccines, which finds application in the medical industry for the production of vaccines against poliomyelitis viruses, rabic viruses, arboviruses, myxoviruses, etc.

Known in the art are methods for the production of vaccines by using ultracentrifuges. Strains A2/England 1/64, B/Rumanien 2/66 or strain $A_2$/Ann Arbor/ 1/57 or any other strain of influenza, antigen types $A_1$, $A_2$ or B, isolated from man, are grown following a standard procedure in the allantoic cavity of 10–11 day old embryos. The allantoic fluid thus produced with titres of 512-2048 haemagglutinating units is clarified by low-speed centrifuging (15 min., 1000g ). Thereafter the supernatant is centrifuged for 60 minutes at 4000 g. The precipitate thus obtained is diluted in an isotonic phosphate buffer and the liquid obtained is subjected to centrifuging in a preparative centrifuge in a density gradient of sucrose.

The fractions having maximum virus content have on the average 5000 haemagglutination reaction units (HA) per mg of protein. This suspension is diluted with isotonic phosphate buffer to 1000-2000 HV per ml. Thereafter the virus suspension is inactivated by adding ethyl ether (1:2) with 1 mg/ml of "Tween-80". The mixture thus obtained is sterilized by filtering through 0.45 mu cellophane membranes to produce the vaccine.

Also known in the art is a method of producing vaccines by resorting to ultracentrifuging, wherein allantoic fluid (pH 7.8 to 8.0) is mixed at a temperature of from 0° to 3° C with sodium oxalate (0.16 mole) and dry barium sulphate, from 40 to 60 g per liter of allanoic fluid. The suspension is stirred for 90 minutes and left overnight. Then the barium sulphate containing the absorbed virus is separated by centrifuging in a centrifuge with a flow-through rotor at 7000 rpm, the flow-rate being 50 to 80 liters/hour. Elution is carried out in 1/7-th of the starting volume using a solvent containing 0.2 weight percent of gelatine, 0.25 mole of citrate, 1.0 mole of NaCl, 0.4 mole of tris (trioxymethylaminomethane) 0.16 mole of Tween-80 at pH = 7.2. Next day the barium sulphate is separated by centrifuging at 800 g for 10 minutes at room temperature. The eluate thus produced is brought to pH = 8.0 and diluted with apyrogenic water, thereafter it is subjected to centrifuging and gel-filtration on Sephadex G-25, and again centrifuged in the sucrose gradient. The samples produced are inactivated with formaldehyde, subjected to bacteriological filtration, and the vaccine is finished.

A disadvantage of the above methods resides in complex technology, including multistep purification and concentration steps, especially concentration by way of adsorption-elution and purification with the help of gel-filtration. The operations described above result in 50 to 90 percent losses of viral material and require sterilization upon completion of the purification and concentration processes.

In obtaining killed vaccines the process of chemical inactivation of the vaccines leads to reduced immunogenity of the viral particles. An attempt to counterbalance this effect involves additional introduction of viral material and consequently more protein which tends to cause undesirable side reaction of the organism.

It can be further pointed out that the above methods require sophisticated equipment.

It is an object of the present invention to improve the processing technology, simplify the equipment required and produce vaccines that do not cause side effects in the organism.

The object is achieved in a method for producing vaccines involving purification and concentration of the viral culture, followed by isolation thereof, wherein according to the invention the purification of a viral culture is carried out mainly by means of gel-chromatography in a column packed with a porous virion non-absorbing silicate material having pore diameter from 50 to 1000 A which is followed by concentration of the suspension, by adsorption and elution, or the initial suspension of vira is concentrated by adsorption-elution and then additionally purified by gel chromatography in a column packed with porous silicate material having pore diameter of 50 to 10000 A, or the starting suspension of vira is subjected only to gel chromatography in a column packed with a porous silicate material having pore diameter of 50 to 10000 A, followed by the production of the vaccine.

In order to produce killed vaccine the viral suspension is inactivated by treating with ultraviolet radiation at a dose of 5000 to 200000 erg/cm$^2$ or with a 5% solution of formaldehyde.

The adsorption-elution procedure is preferably carried out in a column packed with porous silicate material, followed by desorption of the viral culture with buffer solutions having pH 6 to pH 10 and ionic strength of 0.1 to 1.0.

The preferred buffer solution to phosphate buffer having pH value of from 6 to 8.2, or a tris buffer having pH value of 7.2 to 10.0 and ionic strength of 0.1 to 1.0.

The porous material preferably used for the process is sodium-borosilicate glass or large-pore gels of silicic acid having grain size of 0.1 to 0.3 mm and pore diameter of from 300 to 2000 A and porosity of 0.3 to 2.5 cm$^3$/g.

The adsorption-elution concentration of the viral culture is altentatively carried out on formaldehyde-treated erytrocytes.

The vaccine is preferably finished by means of transferring the suspension obtained to physiological conditions characterized by a pH value of 7.0 to 7.3 and NaCl concentration of 0.14 to 0.15 mol/l.

The vaccine is preferably transferred to physiological conditions by means of gel chromatography on a column packed with porous silicate material having pore diameter of from 50 to 10000 A. The porous silicate material most advantageously used is sodium-borosilicate glass or large-pore gels of silicic acid having grain size of 0.1 to 1.0 mm and pore diameter of 300 to 2000 A and porosity of 0.3 to 2.5 cm$^3$/g.

The method according to the present invention is realized as follows:

The viral suspension is purified by gel chromatography.

The viral culture is introduced into a column filled with porous silicate material which is virion non-absorbing having pore diameter of 50 to 10000 A. The operation is preferably carried out on sodium-borosilicate glasses or on large pored gels of silicic acid having grain size of 0.1 to 0.3 mm and pore diameter of 300 to 2000 A and porosity of 0.3 to 2.5 cm$^3$/g.

Said porous silicate materials, owing to their porosity permit efficient separation of viral preparations both from low-molecular and high molecular impurities. Moreover, the gel chromatography step ensures proper conditions for effectively performing further concentration of the viral material. The viral material is concentrated by adsorption-elution.

The adsorption-elution is preferably carried out in a column filled with a porous silicate material which permits to vary the sorption surface within broad limits.

The preferred porous silicate material is sodium-borosilicate glass or large pore gels of silicic acid having grain size of 0.1 to 0.3 mm and pore diameter of 300 to 2000 A, and porosity of 0.3 to 2.5 cm$^3$/g. Sorption is carried out until the sorbent is completely saturated with the virus. The virus is eluted from the sorbent by means of buffer solutions having pH value of 6.0 to 10.0 and ionic strength of from 0.1 to 1.0.

The preferred buffer solutions are phosphate buffer with pH value of 6 to 8.2, or tris buffer with pH value of 7.2 to 10.0 and ionic strength of 0.1 to 1.0.

The adsorption-elution can also be carried out on formalin treated eritrocytes.

Then the vaccine is produced. The vaccine is advantageously finished by transferring thereof into physiological conditions. The operation is preferably carried out with the aid of gel chromatography in a column packed with silicate material.

For certain types of viruses the vaccines can be produced by starting with the step of concentrating the viral material, followed by purification of the viral preparation or it can be achieved in a single stage gel chromatography of the viral suspension.

In order to obtain killed vaccines the purified and concentrated live vaccine is preferably treated by ultraviolet radiation at doses of 5000 to 200000 erg/cm$^2$ or with a 5% solution of formaldehyde.

The method according to the present invention compares favourably with the prior art methods, being distinguished by simple technology and unsophisticated equipment used for the purpose.

The use of silicate materials which are mechanically strong, does not change their properties in the process of sterilization, does not swell, and permits the process to be carried out at high rates. Silicate materials cannot serve as substrates that permit bacterial growth, they regenerate easily and can be used repeatedly. These materials offer a wide range of pore sizes thus ensuring a high degree of efficiency of the gel chromatography process. On the other hand, the sorption capacity of these materials ensures efficient concentration of viral suspensions.

A combination of gel chromatography purification and the sorption concentration of viruses on these materials permits highly effective vaccines to be produced, causing no side effects in the organism.

The ultra violet radiation treatment for producing killed vaccines allows the viral material to be inactivated without affecting the immunogenic properties of the viruses.

The present invention will be better understood by referring to the following examples of embodying the process for the production of vaccines.

EXAMPLE 1

An allanotic culture of influenze virus (Strain $A_2$-/Hongkong 68/), taken in an amount of 840 ml and having a titer of 320 haemagglutinating units is passed through a 3.0 cm diameter 32 cm high column packed with sodium borosilicate glass (0.1 to 0.3 mm grain size, pore diameter of 500 A) at a rate of 0.3 to 0.6 cm/min. The removal of impurities and elution of virus is carried out in steps using tris buffers prepared with pyrogenic water (0.005 to 0.05 mole, pH from 8.2 to 8.6, concentration of NaCl in the range of 0 to 0.5 mole and ionic strength of 0.1 to 1.0 50 to 100% of the virus is contained in 30 ml of eluate having a titer of 10000 haemagglutinating units.

The vaccine is purified, isolated and transferred into the physiological conditions in a diameter 3 cm and 50 cm high column packed with a large-pore gel of silicic acid (grain size of 0.16 to 0.25 mm, pore diameter of 450 A and porosity of 1.3 cm$^3$/g.).

The viral material is eluted with a phosphate buffer solution, 0.02 mole, 7.4 to 7.5 pH, concentration of NaCl 0.85% at a rate of 0.5 cm/min.

About 100 ml of vaccine is thus produced which contains at least 50% of the initial virus.

Comparative characteristics of the starting material and the virus vaccine produced:

|  | Initial material | Vaccine |
| --- | --- | --- |
| Neuraminidaze activity in optical density units, 549 nm wavelength | 0.17 | 0.69 |
| Protein by Zowry's method (mg/ml) | 5.5 | 0.04 |

The virus inactivation in the vaccine is achieved by means of ultra-violet irradiation. The thickness of virus-containing liquid is from 0.1 cm to 0.5 cm, radiation intensity is 380 to 400 erg/mm$^2$.sec., for 5 minutes.

Immunogenic activity was studied on mice by way of a single administration of 0.3 ml of killed vaccine, intraperitoneally, average antihaemagglutinin titer was 1:223. Immunogenic action for human organism was evaluated after administering subcutaneously 0.5 ml of the vaccine to 20 volunteer using jet injectors. The ratio of antibodies increase averaged 17.2, in the absence of any noticeable reactivity.

EXAMPLE 2

An allantoic culture of influenza virus (strain A2 Victoria 36/72 /$H_3N_2$/ having a titer of 640 haemagglutinating units is subjected to gel chromatography in a 3 cm diameter and 50 cm high column filled with sodium-borosilicate glass (grain size from 0.1 to 0.3 mm, pore diameter 1800 A, porosity, 1.6 cm$^3$/g.)

The virus material is eluted with a tris buffer, pH 7.5, concentration of NaCl 0.85 weight percent, at a rate of 0.5 cm/min.

Further, the operations of adsorption-elution and completion of the vaccine are carried out as described in Example 1.

The process yields about 200 ml of vaccine containing about 50 percent of the initial virus.

|  | Initial material | Vaccine obtained |
| --- | --- | --- |
| Neuraminidaze activity | 0.03 | 0.4 |
| Titer of haemagglutinins | 320 | 1280 |
| Protein (mg/ml) | 2.4 | 0.03 |

Inactivation is carried out similarly to Example 1.

The immunogenic activity was studied on mice, similarly to the procedure described in Example 1. The average titer of antihaemagglutinins was 1:275.

EXAMPLE 3

An allantoic culture of influenza virus (USSR strain 69) having 512 haemagglutinating units is concentrated by adsorption-elution on formaldehyde treated erythrocytes. Then the culture is subjected to gel chromatography in a 3 cm diameter and 50 cm high column packed with silicic acid gel (grain size from 0.16 to 0.25 mm, pore diameter 450 A and porosity 1.3 cm$^3$/g), pH 7.5, concentration of NaCl, 0.85 weight percent.

The process yields about 100 ml of vaccine containing at least 50% of the starting virus.

Comparative characteristics:

|  | Initial material | Eluate | Vaccine obtained |
|---|---|---|---|
| Titer of haemagglutinins | 512 | 4196 | 1024 |
| Protein content | 7 mg/ml | 0.7 mg/ml | 0.1 mg/ml |

The immunogenic activity was studied on mice, similarly to Example 1.

The average titer of antihaemagglutinins = 1:300.

EXAMPLE 4

A 10% brain suspension of Bolivian hemorrage fever virus with a starting titer of 1:8 (in the complement fixation reaction) was inactivated by a 5% solution of formaldehyde, then clarified by centrifuging for 20 minutes at 6000 rpm. Thereafter the viral suspension was subjected to gel chromatography in a 0.9 cm diameter 20 cm high column packed with sodium borosilicate glass having pore diameter of 1200 A, porosity 0.88 cm$^3$/g and grain size of from 0.1 to 0.3 mm. The viral material was eluted by means of tris buffer, 0.05 mole, pH 8.5 to 7.5, concentration of NaCl of 0.5 to 0.15 mole, at a rate of 0.5 cm/min.

The process yields about 5 ml of vaccine containing at least 50 percent of the starting virus.

Comparative characteristics of the starting material and the vaccine produced:

|  | Initial material | Vaccine obtained |
|---|---|---|
| Titer (complement fixation reaction) | 1:8 | 1:4 |
| Protein (Loury) (mg/ml) | 7.6 | 0.23 |
| Immunogenic activity (neutralization index, 1g LD$_{50/ml}$ on guinea pigs) | over 3 | over 3 |

EXAMPLE 5

A suspension of rabies virus culture grown on a kidney culture of Syrian hamster having a starting titer 1g over 3, is subjected to gel chromatography in a 0.9 cm diameter 10 cm high column packed with sodium borosilicate glass having pore diameter of 1600 A and porosity of 2.1 cm$^3$/g and grain size of 0.1 to 0.3 mm. The viral material is eluted by means of a phosphate buffer 0.06 mole, 7.5 pH and concentration of NaCl of 0.15 molar, at a rate of 0.5 cm/min.

As a result, one run yielded 1.0 ml of vaccine containing at least 50% of the starting virus.

Comparative characteristics of the starting and purified material:

|  | Initial material | Vaccine obtained |
|---|---|---|
| Titer (on mice), 1g LD$_{50/ml}$ | 6.7 | 6.5 |
| Protein (Lowry), mg/ml | 2.0 | under 0.01 |

The vaccine is inactivated with a 5% solution of forlaldehyde for 24 hours at room temperature.

The immunogenic index of the vaccine thus produced on mice is 1.0.

What is claimed is:

1. A method for producing vaccines comprising purification of a viral culture by gel chromatography in columns packed with a porous silicate virion nonabsorbing material having pore diameter of 50 to 10,000A, concentration by adsorption in columns packed with a porous silicate sorbent having a pore diameter of 50 to 10,000A and a porosity of 0.3 to 2.5 cm$^3$/g, followed by virus desorption by means of buffer solutions having a pH of 6 to 10 in two steps using a gradient of ionic strength of from 0.1 to 1.0:
   a. at the beginning of the gradient, the columns are washed to eliminate the initial culture remaining between the sorbent granules, and
   b. at the end of the gradient, virions are desorbed, with subsequent transfer of the viral suspension into physiological conditions of pH 7 to 7.8 with NaCl concentration of 0.14–0.15 mole/1 and inactivation of the viral suspension.

2. A method as claimed in claim 1, wherein the porous silicate material is a material selected from the group consisting of sodium-borosilicate glass and large-pore gels of silicic acid with a pore diameter of 300 to 2,000A, a porosity of 0.3 to 2.5 cm$^3$/g and a grain size of 0.1 to 0.3 mm.

3. A method as claimed in claim 1, wherein the buffer solution is selected from the group consisting of phosphate buffers with a pH value of 6.0 to 8.2 and tris buffers with a pH value of 7.2 to 10.0.

4. A method as claimed in claim 1, wherein for separation of killed vaccinae the viral suspension is inactivated by ultra-violet irradiation in a dose of 5,000 to 200,000 erg/cm$^2$.

5. A method as claimed in claim 1, wherein said transfer into physiological conditions is effected by gel chromatography in a column packed with a porous silicate material having a pore diameter of 50 to 10,000A.

6. A method according to claim 1, wherein the vaccines are antiinfluenza, antipoliomyelitis, antirabies, antiarboviral, antimyxoviral vaccines.

7. A method for producing vaccines comprising concentration of a suspension of a viral culture by adsorption in columns packed with a porous silicate sorbent having a pore diameter of 50 to 10,000A and a porosity of 0.3 to 2.5 cm$^3$/g, followed by the virus desorption by means of buffer solutions having a pH of 6.0 to 10.0 in two steps using a gradient of ionic strength of from 0.1 to 1.0:

a. at the beginning of the gradient, the column is washed to eliminate the initial culture remaining between the sorbent granules, and
   b. at the end of the gradient, virions are desorbed from the sorbent granule surface; purification by gel-chromatography in a column packed with a porous silicate material having a pore diameter of 50 to 10,000A and granule size of 0.1 to 3 mm, with subsequent isolation of the vaccine by transferring the viral suspension into physiological conditions of pH 7.8 with NaCl concentration of 0.14–0.15 mole/1 and inactivation of the viral suspension.

8. A method according to claim 7, wherein the vaccines are antiinfluenza, antipoliomyelitis, antirabies, antiarboviral, or antimyxoviral vaccines.

* * * * *